United States Patent
Tran

(10) Patent No.: US 10,076,612 B2
(45) Date of Patent: Sep. 18, 2018

(54) GAS CONDITIONING DEVICES

(71) Applicant: Nathanial Tran, Apple Valley, MN (US)

(72) Inventor: Nathanial Tran, Apple Valley, MN (US)

(73) Assignee: LEXION MEDICAL LLC, St. Paul, MN (US)

( * ) Notice: Subject to any disclaimer, the term of this patent is extended or adjusted under 35 U.S.C. 154(b) by 342 days.

(21) Appl. No.: 13/573,861

(22) Filed: Oct. 9, 2012

(65) Prior Publication Data

US 2014/0100517 A1 Apr. 10, 2014
US 2016/0256658 A9 Sep. 8, 2016

Related U.S. Application Data

(60) Provisional application No. 61/627,537, filed on Oct. 13, 2011.

(51) Int. Cl.
| | |
|---|---|
| *A61M 37/00* | (2006.01) |
| *A61M 13/00* | (2006.01) |
| A61M 16/10 | (2006.01) |
| A61M 16/16 | (2006.01) |

(52) U.S. Cl.
CPC ........ *A61M 13/003* (2013.01); *A61M 16/109* (2014.02); *A61M 16/161* (2014.02); *A61M 16/105* (2013.01); *A61M 16/16* (2013.01); *A61M 2202/02* (2013.01); *A61M 2202/0468* (2013.01); *A61M 2205/3331* (2013.01); *A61M 2205/3334* (2013.01); *A61M 2205/3368* (2013.01); *A61M 2205/3379* (2013.01); *A61M 2205/3653* (2013.01); *A61M 2205/50* (2013.01)

(58) Field of Classification Search
CPC .... A61M 13/003; A61M 16/10; A61M 13/00; A61M 16/16; A61M 16/161; A61M 2202/02; A61M 2202/0468; A61M 2205/3368; A61M 2205/3334; A61M 2205/3653; A61M 2205/50; A61M 2205/3379; A61M 2205/3331; A61M 16/105; A61M 16/109; A61M 2205/02
USPC ....... 604/23–26, 65–67; 128/203.27, 200.14; 261/158
See application file for complete search history.

(56) References Cited

U.S. PATENT DOCUMENTS

| | | | |
|---|---|---|---|
| 5,800,381 A | 9/1998 | Ognier | |
| 6,068,609 A | 5/2000 | Ott et al. | |
| 6,299,592 B1 * | 10/2001 | Zander | ............................ 604/26 |
| 2004/0254524 A1 * | 12/2004 | Spearman | ........... A61M 13/003 604/26 |
| 2006/0058731 A1 * | 3/2006 | Burnett | ............... A61M 1/1678 604/29 |
| 2006/0129098 A1 * | 6/2006 | Hart et al. | .................... 604/113 |
| 2009/0184832 A1 * | 7/2009 | Lloyd | ................. A61M 13/003 340/635 |

(Continued)

*Primary Examiner* — Kevin C Sirmons
*Assistant Examiner* — Tiffany Legette-Thompson
(74) *Attorney, Agent, or Firm* — Johnson & Phung LLC

(57) ABSTRACT

A medical gas condition system for supplying a liquid hydration fluid to a hydrator before or during an ongoing medical procedure by coupling the flow of liquid hydration fluid into the hydrator to either the absence of flow of medical insufflation gas into the hydrator or to a condition where the liquid hydration fluid can be absorbed by a hydrator instead of being forced through the hydrator in liquid form.

17 Claims, 2 Drawing Sheets

(56) References Cited

U.S. PATENT DOCUMENTS

2009/0240192 A1* 9/2009 Power ................ A61B 17/3474
  604/26
2010/0241061 A1* 9/2010 Ott ..................... A61B 17/3474
  604/26

* cited by examiner

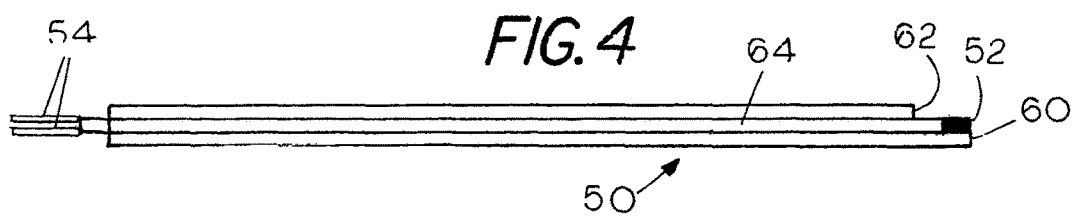

GAS CONDITIONING DEVICES

CROSS REFERENCE TO RELATED APPLICATIONS

This application claims priority from provisional application Ser. No. 61/627,537 filed Oct. 13, 2011.

STATEMENT REGARDING FEDERALLY SPONSORED RESEARCH OR DEVELOPMENT

None

REFERENCE TO A MICROFICHE APPENDIX

None

BACKGROUND OF THE INVENTION

This invention relates generally to medical gas conditioning systems and, more specifically, to a system for supplying hydration fluid to a hydrator in a medical gas conditioning device.

Inflating a patient's body cavity with a medical insufflation gas distends, or inflates, the body cavity producing an operating region within the body cavity, which enables performance of a minimally invasive surgical procedure on the patient. Douglas Ott et al. U.S. Pat. Nos. 5,411,474; 6,068,609 and 7,066,902 show and describe a medical apparatus that humidifies or otherwise conditions an insufflation gas during such a surgical procedure. Briefly, the patents describe the heating and hydrating of the insufflation gas, i.e. the conditioning of the insufflation gas, before injecting the insufflation gas into a body cavity through an inflation device such as a trocar. In order to hydrate the insufflation gas one injects a charge of hydration fluid into a hydrator where the hydration fluid contacts the insufflation gas and humidifies the insufflation gas before injecting the insufflation gas into the patient's body cavity. In addition, one may heat the insufflation gas thereby bringing the insufflation gas to the proper temperature for insertion into the body cavity. During the medical procedure one periodically injects the conditioned insufflation gas into the patient's body cavity through an inflation device such as trocar in order to maintain the body cavity in an inflated condition since some of the insufflation gases escape from the body cavity during the performance of the surgical procedure.

Laparoscopy is an example of one type of a minimal invasive surgery where one inflates a body cavity with a medical insufflation gas. In a laparoscopic surgical procedure, a surgeon manipulates instruments inside a patient's inflated body cavity through a trocar. The most prevalent medical insufflation gas used in the laparoscopic surgical procedures is carbon dioxide, which is directed into a peritoneal cavity through a trocar. A device called an insufflator regulates the delivery of the carbon dioxide gas to the body cavity. Typically, the insufflator receives an unconditioned medical gas from a gas canister containing a medical grade insufflation gas with the gas typically having water vapor concentrations on the order of 200 parts per million, which is extremely dry. In addition to the insufflation gas being dry, the unconditioned insufflation gas delivered from the gas canister is generally at a temperature less than the ambient temperature. In a typical surgical setting the ambient temperature level of the surgical setting may be about 20° C. and the patient's normal body temperature of 37° C., which results in a large temperature difference between the temperature of the unconditioned insufflation gas and the body temperature of the patient. Studies performed over several decades have produced a large body of evidence that shows that the use of unconditioned insufflation gas, such as carbon dioxide, in laparoscopic surgical procedure results in adverse effects for the patient. However, by conditioning the insufflation gas, with respect to both its temperature and relative humidity, reveals that one can avoid the adverse effects that occur with unconditioned insufflation gas.

As it was assumed that conditioning of the insufflation gas did not provide a physiological benefit to the patient the early medical devices transporting the insufflation gas from the insufflator to the patient consisted of a length of plastic tubing with an inline filter attached to the tubing to block unwanted contaminates from the source of the insufflation gas. Since no conditioning was performed to the insufflation gas the body cavity of the patients was inflated with a cold dry gas. The insufflation systems have evolved to the current state where an insufflation devices can both warm and humidify an insufflation gas such as carbon dioxide gas although other insufflation gases may also be warmed and humidified. Such insufflation systems may increase the moisture content of the gas to near 100% relative humidity. Such gas conditioning systems, which are shown in U.S. Pat. Nos. 5,411,474 and 6,068,609, have resulted in physiological benefits to the patient.

The benefits of insufflation systems, which conditions the insufflation gas, reveal that certain operational requirements of the insufflation system may require disruptions of the medical procedure or at least cause inconveniences. For example, the medical personal may need to separately introduce the hydration fluid into a hydrator in order to hydrate the insufflation gas before the surgical inflation gas flows into the patient's body cavity. Typically, the hydration fluid needs to be introduced into the hydrator before the surgical procedure begins and periodically during the surgical procedure. For example, after an initial hydration of the hydrator, one may add hydration fluid to the hydrator after a threshold condition such as 150 liters of insufflation gas have passed through the hydrator with the threshold condition based on a determination that shows the hydrator can hold sufficient hydration fluid to hydrate at least 150 liters. While the task of periodically supplying hydration fluid to the hydrator does not present an onerous task for medical personnel it has the potential to be accidentally overlooked during the surgical procedure resulting in unhydrated insufflation gas being supplied to the patient. Therefore an apparatus and method that can automatically supply a hydration fluid into the existing hydrators, which may be done on-the-go, would provide a benefit to the medical staff and the patient. Another inconvenience with the existing hydration systems is that, the supply of medical gas to the hydrator needs to be suspended or shut off when supplying the hydration fluid to the hydrator in order to prevent the hydration fluid from being forced through the hydrator and into the patient's body cavity without having an opportunity to being absorbed by the hydration member in the hydrator. The failure of the hydrator to absorb the hydration fluid may have adverse effects including accumulation of fluid on the lens of a visualization device, which is used to during the medical procedure, thereby obstructing the surgeons view of the surgical site.

SUMMARY OF THE INVENTION

The invention comprises a method and an apparatus for supplying liquid hydration fluid to a hydrator in a medical gas conditioning system either before or during a medical procedure with the system that may include a sensor for determining a flow condition of the insufflation gas and a controller for initiating the injection of the liquid hydration fluid into a hydrator during flow conditions where the liquid hydration fluid can be absorbed by the hydration media in the hydration chamber to prevent the insufflation gas from carrying the liquid hydration fluid through the insufflator. The supplying of liquid hydration fluid may be based on time intervals where there is an absence of insufflation gas flowing into the hydrator thus enabling the liquid hydration fluid to be absorbed by the hydrator without the insufflation gas accidentally forcing the liquid hydration fluid through the hydrator.

A feature of the invention is that the liquid hydration fluid may also be supplied during a flow of insufflation gas into a hydrator if the flow of insufflation gas is below a critical condition.

A feature of the system is that the liquid hydration fluid may be automatically supplied to the hydrator prior during a medical procedure without the need to monitor the amount of liquid hydration fluid in the hydrator.

Further features of the inventions are that the time periods for supplying of hydration fluid may be limited to occur only after a threshold condition has occurred such as after an initial volume of insufflation gas has been delivered to the hydrator.

BRIEF DESCRIPTION OF THE DRAWINGS

FIG. 4 is a side view of a multilayer media in an unwound condition.

DESCRIPTION OF THE PREFERRED EMBODIMENT

Figure 1:
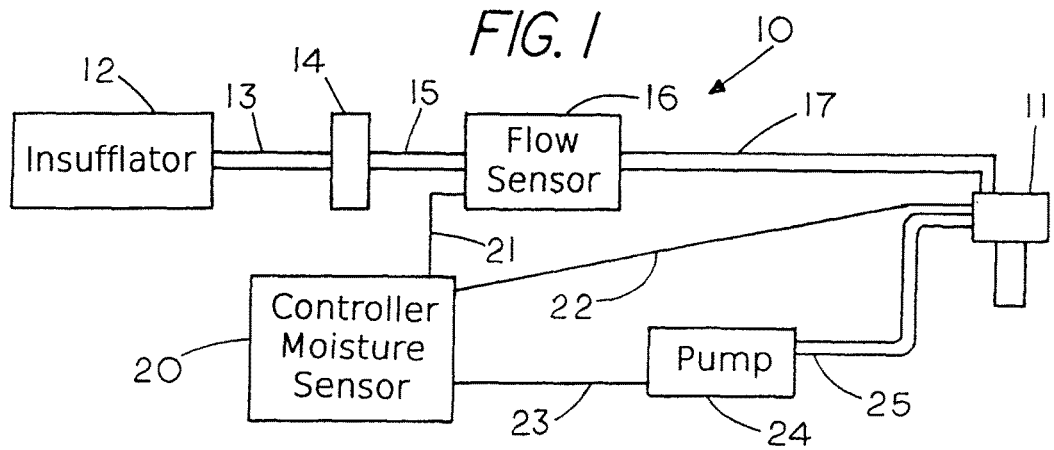
FIG. 1 is a block diagram of a system for on-the-go hydration of a gas conditioning device.
Figure 2:
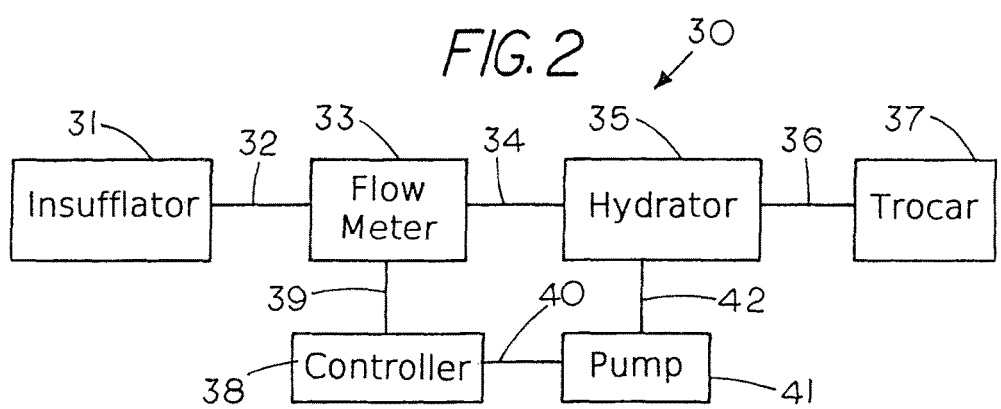
FIG. 2 is a block diagram of a system for on-the-go hydration of a gas conditioning device.

FIG. 1 and FIG. 2 show examples of two types of systems capable of supplying hydration fluid to gas conditioning devices, which have a hydrator for hydrating an unconditioned insufflation gas. The systems may include on-the-go hydration and on-the-go heating of an unconditioned insufflation gas in the gas conditioning device.

FIG. 1 shows an example of a system where the gas conditioning device is located in a trocar 11. In this type of system the trocar contains a hydrator or a hydration chamber for receiving both a hydration fluid and an unconditioned insufflation gas. An insufflation system where the trocar has a hydrator for heating and hydrating an unconditioned insufflation gas is shown in pending U.S. patent application titled GAS CONDITIONING TROCAR, Ser. No. 12/381,978 filed Mar. 18, 2009 and is hereby incorporated by reference.

FIG. 2 shows an example of a system where the hydrator 35 is located outside the trocar 37 with the hydrator receiving insufflation gas from an insufflator 31. An example of such a hydrator is the Insuflow Device®, which is sold by Lexion Medical of St. Paul, Minn. The device is shown and described in Ott et al U.S. Pat. Nos. 5,411,474; 6,068,609 and 7,066,902 which are hereby incorporated by reference.

In either system it may be necessary to replenish the hydration fluid in the hydrator either before or during a medical procedure by injecting additional hydration fluid into the hydrator.

Referring to FIG. 1, the system 10 maintains the conditioning of an insufflation gas during a medical procedure by intermittently replenishing the hydration fluid in the hydrator, which is located in the gas conditioning trocar 11. Typically, the medical procedure is endoscopy and more specifically laparoscopy. The invention may also be used during thoracoscopy as well as other medical procedures. The system 10 may include a heater and hydrator in trocar 11 for heating and hydrating an insufflation gas delivered from an insufflator 12, which supplies an insufflation gas to the heater and hydrator as needed. In some embodiments, the heater and hydrator in the trocar 11 may be replaced by a hydrator alone. Typically, a hydrator contains a hydrophilic media to absorb a liquid hydration fluid to enable the hydration fluid to enter a vapor phase, which causes humidification of the insufflation gas flowing through the hydrator.

In system 10 a source of medical gas may be located in or connected to insufflator 12. The insufflator 12 may contain a flow or pressure regulator or other device to control the delivery of an unconditioned medical gas, such as carbon dioxide, to an insufflation device 11 although the system may be used with other insufflation gasses. The medical insufflation gas may be delivered through a continuous flow of insufflation gas into the inflation device 11 or through repeated pulses of insufflation gas into the inflation device 11. In either case one needs to maintain the pressure in the cavity of the patient to sustain the medical procedure. During the inflation process the insufflation gas flows through a filter 14 which removes unwanted containments from the medical gas and a flow sensor 16, which measures the volumetric flow of medical gas therethrough, as well as through various lengths of flexible tubing 13, 15 and 17 that are connected between the various components of the system 10 to thereby provide a closed fluid path between the medical gas in insufflator 12 and the inflation device such as a trocar 11, which extends at least partially into a body cavity of a patient.

System 10 includes a hydrator or gas conditioning chamber, which is located in the inflation device 11, with the hydrator having a liquid absorbing member, such as a hydrophilic member, for receiving and holding a hydration fluid proximate the insufflation gas to enable humidification of the insufflation gas during its presence proximate the hydration fluid. In some instance a heating element may be present in the gas conditioning chamber so the insufflation gas can be both heated and hydrated while in the gas conditioning chamber.

System 10 may also include a controller or microprocessor 20, which connects to a flow sensor 16 through an electrical lead 21, with the controller 20 responsive to flow conditions in flow sensor 16 to enable the controller 20 to recognize the presence or absence of the flow of medical insufflation gas into the insufflation device 11. Flow sensor 16 may be a flow meter or any other type of device that can determine if an insufflation gas is flowing therethrough. An electrical lead 22 connects controller 20 to a moisture sensor (not shown), which is located in the trocar 11. The moisture sensor measures the conditioning level of the insufflation gas in the trocar 11. If the conditioning level of the insufflation gas is below an acceptable level the controller 20 can be readied for the process of supplying hydration fluid to the hydration chamber in trocar 11. An electrical lead 23 connects controller to a pump 24, which contains a source of hydration fluid or is connected to a source of hydration fluid that can be delivered to the hydrator. A conduit 25 for delivery of the hydration fluid from pump 24 to trocar 11 connects the output of pump 24 to a hydrator located in a hydration chamber in trocar 11. While a moisture sensor may be used to measure the conditioning level of the insufflation gas in some cases the moisture sensor may be eliminated.

In operation of the system shown in FIG. 1 flow sensor 16 measures the volumetric flow of medical insufflation gas flowing through line 17 while a moisture sensor in a gas conditioning trocar 11 determines whether the moisture content of the insufflation gas is sufficient. Both the flow and the moisture content of the insufflation gas may be monitored by controller 20. If the controller 20 determines an absence of insufflation gas flowing through flow sensor 16 and the moisture content of the insufflation gas is insufficient or below a predetermined level the controller 20 activates pump 24 which pumps liquid hydration fluid into a hydration chamber in trocar 11. If the flow sensor determines that insufflation gas is flowing into trocar 11, the controller 20 stops pump 24 to prevent pumping liquid hydration fluid into the hydration chamber in trocar 11, thus avoiding a condition where liquid hydration fluid may be forced through trocar 11 before the liquid hydration fluid has had time to be absorbed by the hydration chamber media, such as a hydrophilic media in the hydration chamber of the trocar.

The controller 20, which can terminate the administration of liquid hydration fluid into the hydration chamber of trocar 11 when insufflation gas flow is present, can also be used in an alternate mode to allow simultaneous flow of liquid hydration fluid and insufflation gas under certain determinable conditions described herein.

During a simultaneous flow of hydration fluid and insufflation gas from the insufflator, the controller 20 can automatically terminate, or limit, the delivery of the liquid hydration fluid to the hydration chamber before the liquid hydration fluid flows directly through the hydration chamber of trocar 11.

Depending on various factors, which are generally unique to an insufflation device, the liquid hydration fluid can be safely injected into the hydration chamber of trocar 11 as insufflation gas flows through the hydration chamber, if one avoids undesirable encapsulation or entrainment of the liquid hydration fluid droplets in the insufflation gas (i.e. the fluid remains in a liquid state in the stream of insufflation gas). Such an on-the-go system for simultaneous injection of liquid hydration fluid and insufflation gas is useful where it is anticipated that the flow of insufflation gas is substantially continuous with only limited interruptions.

The medical insufflation gas flow condition where the hydration chamber can be hydrated on-the-go is generally specific to the type of insufflator and the type of hydration fluid, however, the personnel operating the insufflator can perform a preoperative field test to readily determine critical conditions typically, i.e. conditions such as the volume and flow rate of the hydration fluid where the liquid droplets of hydration fluid flow directly into a patient's body cavity. For example, prior to initiating a medical procedure a medical professional turns on the insufflation gas and at the same time injects hydration fluid at an ever-increasing rate into the hydration chamber of trocar 11. When the person observes that the liquid hydration fluid flows through the hydration chamber of trocar 11 without being absorbed by the hydration chamber media, the person notes the critical flow condition that causes the liquid hydration fluid to be carried through trocar 11 without being fully absorbed by the hydration chamber media. The operator then sets the controller to automatically limit or cease injection of hydration fluid prior to the occurrence of the critical flow condition.

Thus, a feature of the invention is coupling the delivery of liquid hydration fluid to a condition where there is no flow of medical insufflation gas, which allows one to supply liquid hydration fluid to the hydration chamber of trocar 11 without accidentally forcing liquid hydration fluid through the hydration chamber before the liquid hydration fluid can be absorbed by the hydration chamber media.

A further feature of the invention is that the controller 20 can be set to automatically initiate and terminate the delivery of the liquid hydration fluid to the hydration chamber during simultaneous flow of medical insufflation gas and the liquid hydration fluid into the hydration chamber if the flow of medical insufflation gas is such that the liquid hydration fluid can not be readily absorbed by the hydration chamber media. The critical conditions for setting the controller can be determined by an on-the-go field test by the medical personnel. Additionally, worst case conditions may be preset into controller 20 by the manufacturer, taking into account worst case flow conditions involving the most widely used and accepted insufflators currently available 12.

Thus the controller 20 can be set to automatically initiate and terminate the delivery of the liquid hydration fluid to the hydration chamber of trocar 11 during a condition of no flow of insufflation gas into the hydrator or during a flow of insufflation gas. In either case controller 20 can prevent liquid hydration fluid from flowing directly through the trocar in the form of liquid droplets or the like.

An example of a suitable type of hydration pump for intermitting supplying hydration fluid is a servo driven syringe pump although other means or pumps may be used for delivery of the hydration fluid during time specified intervals including peristaltic pumps, pressure cuffs, screw driven syringe pumps and other means that can periodically deliver small volumes of hydration fluid. With use of a servo driven syringe pump an initial volume of hydration fluid is introduced into the syringe pump 24, which is connected to the controller or microprocessor 20, which determines when the hydration fluid in the pump 24 should be injected into the hydrator 11.

The flow sensor or flow meter 16 indicates when the insufflation gas is in a flow condition or a no flow condition in conduit 17. In response to a no flow condition and in some cases other threshold conditions the controller or microprocessor 20 activates the hydration pump 24 to deliver hydration fluid to the hydration chamber in trocar 11. In order to avoid over supplying of hydration fluid to the hydration chamber controller 20 can be set to only activate the pump 24 when additional system threshold conditions are met. For example, the total volume of insufflation gas that is supplied to the insufflation device 11 after initiating of the surgical procedure may be a threshold condition. That is, the controller 20 may not activate pump 24 until a minimum amount of insufflation gas has been consumed. This type of threshold condition depends on the volumetric capacity of the hydration chamber in the insufflation device to hold an initial charge of hydration fluid, which is sufficient to humidify a predetermined volume of dry insufflation gas. For example, a hydrator may have a hydration chamber that has the capacity to contain sufficient liquid hydration fluid to hydrate only 150 liters of an insufflation gas, consequently, before the 150 liters of insufflation gas have been consumed additional hydration fluid needs to be supplied to the hydration chamber in order to replenish the hydration fluid for continuing the hydration of the insufflation gas. Thus a threshold condition may be based on the amount or volume of insufflation gas that has been consumed during the insufflation process. For example, one may want to initiate the supply of hydration fluid to the hydrator after half of the determined amounts of insufflation gas has been consumed.

Another threshold condition where the controller may be prevented from activating the pump may be based on elapsed time. Sill another threshold condition may be relative humidity of the insufflation gas, for example if the hydrator 11 includes a humidity sensor the controller 20 may be programmed to not activate the pump 24 until the humidity of the insufflation gas falls below 100% relative humidity or a predetermined conditioning level. Other threshold conditions may be included based on the needs of the system. Thus, a benefit of the existing system is that the liquid hydration fluid can be supplied to the hydration chamber of the trocar under a variety of conditions without concern for injecting too little or too much hydration fluid into the system. That is the liquid hydration fluid can be supplied before the medical procedure begins, during the medical procedure or on-the-go with the delivery of hydration fluid automatically limited to those time periods when the delivery of the insufflation gas does not adversely affect the operation of the system or would harm the patient.

A further benefit of the hydration system 10 is that it avoids human errors, which may be caused by a failure of the medical staff to notice that the liquid hydration fluid in the hydration chamber has been depleted. In addition, since the system can hydrate the insufflation gas without the assistance of any medical staff it frees the medical staff to attend to other critical matters during the medical procedure.

A further benefit of the hydration system 10 is that during an on going medical procedure it eliminates supplying liquid hydration fluid to the hydration chamber in the trocar 11 during times which may be inconvenient for the medical staff. It should be pointed out that while various factors or threshold conditions have been identified to protect the system 10 from introducing excess hydration fluid into the hydration chamber in trocar 11 still other conditions may be monitored to further limit the times when one can supply hydration fluid to the hydration chamber in trocar 11 without departing from the spirit and scope of the invention.

FIG. 2 is a block diagram of another system 30 for on-the-go hydration of an insufflation gas. In this example the system 30 includes an insufflator 31 having a source of medical insufflation gas 31, a flow meter 33, a hydrator 35, which is separate from a trocar 37, a controller or microprocessor 38 and a pump 41. During the operation of the system 30 the insufflation gas emanating from insufflator 31 flows through a conduit 32 and through flow meter 33. The insufflation gas then flows through a conduit 34 into a hydrator 35 where the insufflation gas is hydrated. The hydrated insufflation gas then flows into trocar 37 through conduit 36. In this example, in contrast to the system of FIG. 1, the hydrator 35 is separate from the trocar 37. The flow of insufflation gas into a hydration chamber (not shown) in hydrator 35 may depend on various factors including the downstream pressure of the insufflation gas in the body cavity with the flow of insufflation gas controlled by a flow regulator in the insufflator 31 or through a feed back system that includes a pressure sensor in the trocar to monitor the actual gas pressure in the patient's body cavity. For example, if the insufflation gas pressure in the patient's body cavity is within a prescribed range no fresh insufflation gas flows into the hydrator 35 on the other hand if the insufflation gas pressure in the patient's body cavity is to low the insufflation gas flows into the hydrator 35 from the source of medical gas in insufflator 31. The presence of a flow condition or a no flow condition of the insufflation gas can be sensed by the controller 38. Once controller 38 determines the insufflation gas is in a no flow condition the controller 38 can activate pump 41 which delivers the hydration fluid to the hydrator 35 until such time as the insufflation gas in the hydrator 35 is hydrated, the insufflation gas begins to flow into the hydrator, or some other condition when hydration would not be beneficial. While the system has been described as capable of injecting hydration fluid when the insufflation gas is in a no flow condition in some cases the insufflation gas may be introduced under low flow conditions, that is a conditions where the flow of insufflation gas is so low that the hydration fluid can be timely absorbed in the hydration chamber without passing directly through the hydrator 35.

While the systems described herein are capable of on-the-go delivery of hydration fluid to a hydrator during a medical procedure the systems may also be used to supply hydration fluid to a hydrator during a non on-the-go condition, for example prior to initiating a medical procedure that requires insufflation of a body cavity or during pauses in the surgical procedure.

Figure 3:
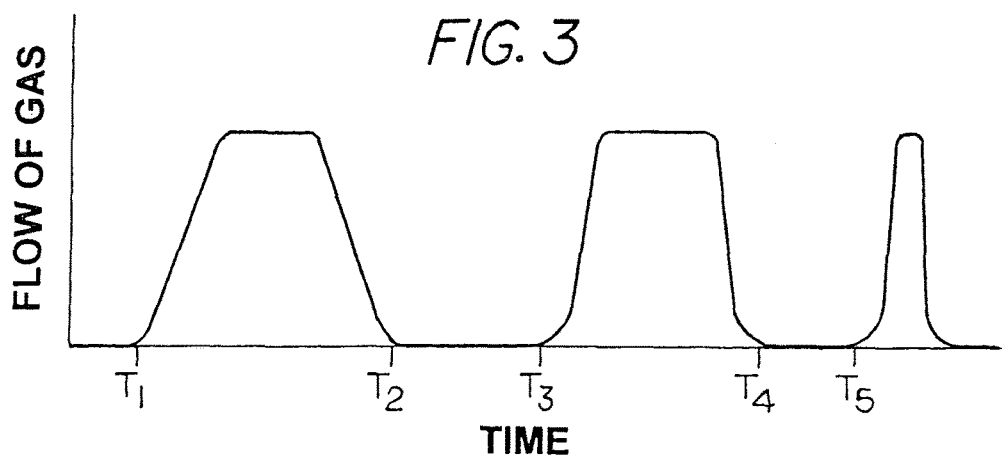
FIG. 3 is graph of the flow of insufflation gas into a hydrator as a function of time.

To illustrate the limited and timely delivery of hydration fluid to a hydrator where there is no flow of insufflation gas reference should be made to FIG. 3, which shows a graph of the flow of an insufflation gas from insufflator 31 into hydrator 35 as a function of time. The graph shows that during the initial period $T_1$ no insufflation gas is supplied to hydrator 35. Starting at time $T_1$, a pulse of insufflation gas flows into the hydrator 35 until time $T_2$ at which time the insufflation gas ceases to flow until time $T_3$ when another pulse of insufflation gas is injected into the system with the insufflation gas ceasing to flow after the time $T_4$. It is during the time period between $T_2$ and $T_3$ and the time period between $T_4$ and $T_5$ i.e. where the insufflation gas is not flowing, that the controller 38 that one can safely inject hydration fluid into the hydrator 35 without accidentally forcing the liquid hydration fluid through the hydrator 35 and into the gas line 36 before the liquid hydration fluid can be vaporized and absorbed by the insufflation gas. Thus a feature of the invention is that controller 38 or controller 20 can initiate and terminate the delivery of the liquid hydration fluid to the hydrator during time intervals of no flow of medical insufflation gas into the hydrator to prevent or inhibit accidentally forcing the liquid hydration through the hydrator. Thus, as illustrated in FIG. 3 a pump 24 or 41 can deliver charges or pulses of liquid hydration fluid between pulses or charges of the insufflation gas. The pulses may be of varying duration and or varying intensity depending on the hydration system as well as the need for hydration of the insufflation gas. In some cases the termination of the delivery of liquid hydration fluid may be based on a maximum time period and in other cases the delivery of liquid hydration fluid may terminate upon the sensor determining that the liquid hydration fluid being delivered to the hydrator is not being absorbed by the hydrator.

In still other methods the deliver of liquid hydration fluid to the hydrator 35 may be directly coupled to the delivery of insufflating gas to the inflation device. Thus, when the system 10 or 30 is supplying insufflation gas to the hydrator, for example, between the times $T_1$ and $T_5$ the controller 38 or 20 prevents delivery of liquid hydration fluid to the hydrator by incapacitating the pump 24 or 41. In this example the controller 20 or 38 may be responsive to the activity of the insufflator 12 or 31 rather than a conditioning level down stream of the insufflator. In this case the supplying of liquid hydration fluid is coupled to the activity of the insufflator. To avoid over hydration of the hydrator one may limit the liquid hydration fluid supplied based on the amount of insufflation gas supplied to the inflation device.

In some cases one may simultaneously supply a pulse or charge of insufflation gas to the hydrator and a pulse or charge of hydration fluid to the hydrator with the pulse or charge of hydration fluid supplied to the hydrator during a period when the pulse or charge of insufflation gas is insufficient to force the hydration fluid through a hydration member. In other cases one may couple the pulse or charge of hydration fluid into the hydrator to the absence of a pulse or charge of medical insufflation gas flowing into the hydrator so that liquid hydration fluid flows into the hydrator only when no insufflation gas flows into the hydrator.

Thus method may include powering a hydration fluid pump 41, 24 during a period when the flow of insufflation gas is insufficient to force the liquid hydration fluid through a hydration member before the liquid hydration fluid can be absorbed by the hydration member by coupling the flow of liquid hydration fluid into the hydrator to the absence of a pulse of medical insufflation gas into the hydrator. It will be apparent that other methods and apparatus may be employed to limit the delivery of liquid hydration fluid without departing from the spirit and scope of the invention described herein. For example, the controller may intermittently deliver liquid hydration fluid to the hydrator in response an absence of a flow of insufflation gas.

As described herein one feature of the invention is a method of automatically hydrating an insufflation gas during a medical procedure without forcing liquid hydration fluid through a trocar and into a patient by supplying a medical insufflation gas to the hydrator, monitoring the flow of medical insufflation gas to the hydrator; and supplying the liquid hydration fluid to the hydrator during a time period where there is an absence of medical insufflation gas flowing into the trocar to thereby rehydrate the hydrator without accidentally forcing liquid hydration fluid through the trocar. By doing so one can deliver the medical insufflation gas containing hydration fluid in vapor form within the insufflation gas.

In the example shown in FIG. 4, the materials of multilayer media 50 include a layer of gas transfer material comprising netting 62 and a layer of fluid transferring material comprising hydrophilic material 60 with a heater assembly 64 extending therebetween. Heater assembly 64 includes a temperature sensor 52 on one end and a pair of electrical leads 54 on the opposite end for connection to a power source.

I claim:

1. A medical gas conditioning system for introducing an insufflation fluid in a gaseous state rather than a liquid state into a patient comprising: a trocar; a hydrator located in the trocar; a source of medical insufflation gas; a sensor for detecting a flow condition of the medical insufflation gas into the hydrator; a source of liquid hydration fluid; a liquid absorbing member in said hydrator for receiving and holding the liquid hydration fluid proximate the medical insufflation gas to enable humidification of the medical insufflation gas during its presence proximate the liquid hydration fluid; and a controller automatically responsive to the sensor, said controller coupling a delivery of the liquid hydration fluid to a delivery of the medical insufflation gas through activating a hydration fluid pump for the delivery of the liquid hydration fluid during the flow condition where there is an absence of the flow of the medical insufflation gas into the hydrator, said controller terminating the hydration fluid pump operation for stopping the delivery of the liquid hydration fluid to the hydrator during the flow condition where there is flow of the medical insufflation gas into the hydrator, and said controller limiting or terminating the delivery of the liquid hydration fluid at or prior to a pre-determined critical flow condition wherein the liquid hydration fluid flows directly into the patient to thereby prevent the liquid hydration fluid from being forced through a the trocar and into the patient before the liquid hydration fluid is vaporized and absorbed by the medical insufflation gas.

2. The medical gas conditioning system of claim 1 wherein the pre-determined critical flow condition occurs when an absorption rate of the liquid hydration fluid into the hydrator is insufficient to prevent entrainment of the liquid hydration fluid by the medical insufflation gas flowing through the hydrator.

3. The medical gas conditioning system of claim 1 wherein the controller activates the hydration fluid pump after a predetermined amount of the medical insufflation gas has been supplied to the hydrator.

4. The medical gas conditioning system of claim 1 wherein the hydrator is located in a gas conditioning trocar and the sensor for detecting the flow condition of the medical insufflation gas is a flow meter and the liquid absorbing member is a hydrophilic.

5. The medical gas conditioning system of claim 1 where the insufflator delivers pulses of the medical insufflation gas to the hydrator and the controller delivers pulses of liquid hydration fluid to the hydrator between pulses of the medical insufflation gas to the hydrator.

6. The medical gas conditioning system of claim 1 wherein the hydrator contains a humidity sensor or a moisture sensor and the delivery of the liquid hydration fluid occurs on-the-go and in response to a signal from the humidity sensor or the moisture sensor.

7. The medical gas conditioning system of claim 1 wherein the controller intermittently delivers the liquid hydration fluid to the hydrator in response to the flow condition where there is an absence of the flow of the medical insufflation gas in the system and in response to inactivation of the insufflator.

8. A medical gas hydration system for introducing an insufflation fluid in a gaseous state rather than a liquid state into a patient comprising: a hydrator located in a trocar for hydrating a medical insufflation gas; a sensor for determining a flow of the medical insufflation gas flowing into the hydrator; a controller coupled to the flow of the medical insufflation gas for terminating the flow of a hydration fluid when the hydration fluid flows in liquid droplets through the hydrator; and a pump controlled by the controller for delivering the hydration fluid to the hydrator during a period when there is an absence of flow of the medical insufflation gas into the hydrator and during a period when the flow of the medical insufflation gas is insufficient to force the hydration fluid in a liquid form through the hydrator.

9. The medical gas hydration system of claim 8 wherein the controller delays the delivery of the hydration fluid until the occurrence of a threshold condition wherein the threshold condition comprises one or all of the following: a predetermined volume of the medical insufflation gas has been supplied to the hydrator, a measurement of a relative humidity of the medical insufflation gas is less than a predetermined conditioning level and a predetermined time has elapsed since initiating the hydration of the hydrator.

10. The medical gas hydration system of claim 8 including an insufflator for delivering the medical insufflation gas and a pump for delivering the hydration fluid where the hydration fluid is delivered before or after delivering the medical insufflation gas to the hydrator.

11. A method of automatically hydrating an insufflation gas during a medical procedure without forcing a hydration fluid through a hydrator comprising:
   intermittingly supplying a medical insufflation gas to the hydrator;
   monitoring a flow of medical insufflation gas to the hydrator; and
   coupling the supply of the hydration fluid to the flow of medical insufflation gas by supplying the hydration fluid to the hydrator in a trocar by activating a pump during a time period where there is an absence of the flow of the medical insufflation gas into the hydrator to thereby rehydrate the hydrator without forcing the hydration fluid in a liquid form through the hydrator.

12. The method of claim 11 wherein the step of supplying the hydration fluid occurs after consumption of a fixed amount of the medical insufflation gas.

13. The method of claim 11 wherein the step of supplying the hydration fluid is in response to a decrease in a relative humidity of the medical insufflation gas.

14. The method of claim 11 wherein the hydration of the medical insufflation gas is done on-the-go and the hydrator receives pulses of the hydration fluid between pulses of the medical insufflation gas into the hydrator.

15. The method of claim 11 including supplying a charge of the medical insufflation gas to the hydrator and a charge of the hydration fluid to the hydrator with the charge of the hydration fluid supplied to the hydrator during a period when the charge of insufflation gas is insufficient to force the hydration fluid through a hydration member or by coupling the charge of hydration fluid into the hydrator to the absence of the charge of the medical insufflation gas into the hydrator.

16. A method of automatically hydrating a medical insufflation gas during a medical procedure without forcing a liquid hydration fluid through a trocar comprising: a supplying of the a medical insufflation gas to a hydrator located in a the trocar; monitoring a flow of the medical insufflation gas to the hydrator; and a pumping of the liquid hydration fluid to the hydrator during the supplying of the medical insufflation gas to the hydrator by coupling a flow of the liquid hydration fluid to the flow of medical insufflation gas by pumping the liquid hydration fluid at a flow rate such that the liquid hydration fluid is absorbed by a liquid absorbing member in a chamber of the hydrator and held proximate the medical insufflation gas in the chamber to humidify the medical insufflation gas without forcing the liquid hydration fluid in a liquid form through the trocar.

17. The method of claim 16 including the step of determining critical flow by visually observing when the particles of the liquid hydration fluid are carried through the medical insufflation gas condition system without being absorbed by the hydrator.

* * * * *